United States Patent [19]

Sekiguchi et al.

[11] Patent Number: 4,697,895
[45] Date of Patent: Oct. 6, 1987

[54] AUTOMATIC OPTOMETER

[75] Inventors: Kyoji Sekiguchi, Tokyo; Yoshimi Kohayakawa, Yokohama, both of Japan

[73] Assignee: Canon Kabushiki Kaisha, Tokyo, Japan

[21] Appl. No.: 741,274

[22] Filed: Jun. 4, 1985

[30] Foreign Application Priority Data

Jun. 12, 1984 [JP] Japan ................................ 59-120137

[51] Int. Cl.⁴ .............................................. A61B 3/02
[52] U.S. Cl. .................................... 351/243; 351/237
[58] Field of Search ................ 351/237, 243, 222, 223

[56] References Cited

U.S. PATENT DOCUMENTS 3,861,790 1/1975 Tamura ................................ 351/243
3,969,020 7/1976 Lynn .................................... 351/237
4,105,302 8/1978 Tate ..................................... 351/237

Primary Examiner—Rodney B. Bovernick
Attorney, Agent, or Firm—Fitzpatrick, Cella, Harper & Scinto

[57] ABSTRACT

An automatic optometer provided with a first visual target for measuring the visual power of a subject, a response input unit for the subject to input a response corresponding to the visual target, a control unit for determining the accuracy of the subject's response input and for presenting additional different visual targets, a counter, the counter being reset each time a visual target is presented, a comparison unit for comparing the output of the counter with a predetermined value, and request means for requesting the subject's response input in accordance with the output of the comparison unit.

9 Claims, 8 Drawing Figures

AUTOMATIC OPTOMETER

BACKGROUND OF THE INVENTION

1. Field of the Invention

This invention relates to an automatic optometer which presents a plurality of visual targets to a subject while changing over the visual targets and measures the subject's visual acuity from the correction of the subject's response input.

2. Description of the Prior Art

In an automatic optometer of this type, a system has heretofore been adopted whereby when a subject's response input is not entered within a predetermined time, a visual target is advanced to the next step to shorten the examination time and to give the examination more continuity. However, this has been inconvenient because it is difficult for the subject to determine that a predetermined time has elapsed.

Further, even there is an inadvertent or erroneous operation in the subject's response input, it is judged as "wrong" in the apparatus because there is no correcting means, and re-examination is effected with the visual acuity value being reduced by one stage. This this has led to a disadvantage in that a correspondingly longer measuring time is required.

SUMMARY OF THE INVENTION

It is an object of the present invention to overcome such disadvantages peculiar to the apparatus of the prior art and to provide an automatic optometer in which when the subject's response input is not entered within a predetermined time, the response input is automatically requested and even if there is an erroneous operation in the subject's response input, it can be immediately corrected so that continuity in examination can be quickly accomplished.

It is also an object of the present invention to provide an automatic optometer which enables measurement of the visual acuity to be automatically effected along a predetermined program while requesting it at each predetermined time.

DESCRIPTION OF THE PREFERRED EMBODIMENT

Figure 1:
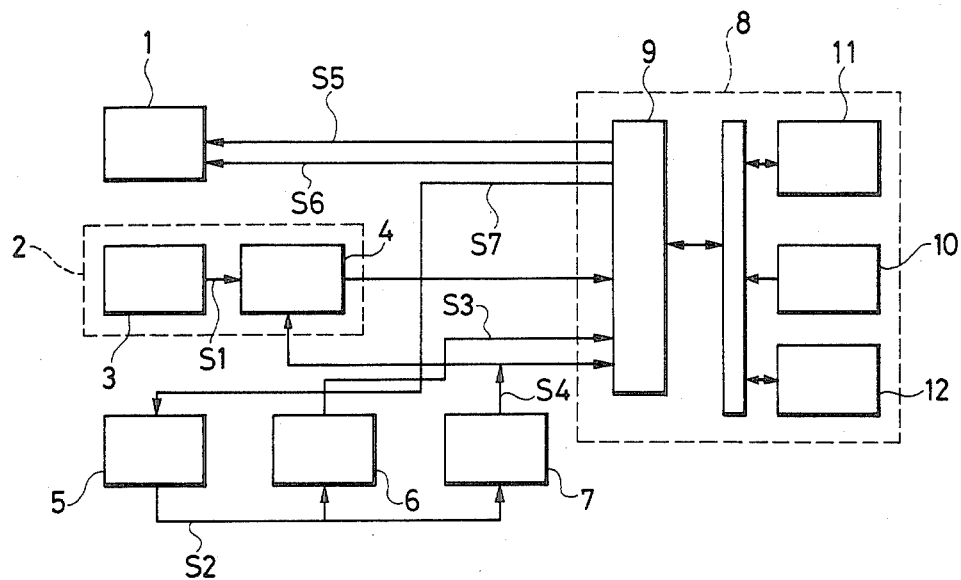
FIG. 1 shows the construction of a block circuit.
Figure 2:
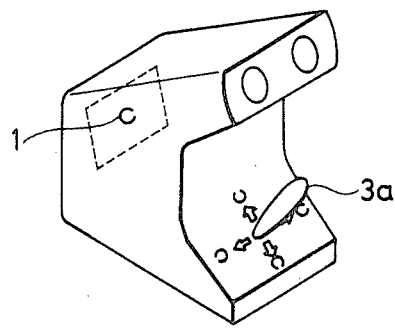
FIG. 2 shows the appearance of the apparatus of the present invention.

Referring to FIG. 1 which shows the construction of an automatic optometer according to the present invention, reference numeral 1 designates a visual target presented to a subject, and reference numeral 2 denotes a response input device by which the subject inputs correspondingly to the visual target 1 presented. The response input device comprises an input switch unit 3 and a memory unit 4, and is designed such that the content of the memory unit 4 is renewed each time an input data signal S1 from the input switch unit 3 enters the memory unit. The input switch unit 3 is connected to a joy stick 3a shown in FIG. 2. Reference numeral 5 designates a counter which is reset and starts to count time each time the visual target 1 is presented. The count data signal S2 of this counter 5 is input to a first comparison unit 6 and a second comparison unit 7. The first comparison unit 6 and the second comparison unit 7 are designed to put out coincidence signals S3 and S4, respectively, when the counter 5 puts out, for example, 2.5 seconds and 3 seconds, respectively. These coincidence signals S3 and S4 and the input data from the aforementioned response input device 2 are input to the interface section 9 of a microcomputer system 8. The microcomputer system 8 is comprised of an ROM (read only memory) 10 in which a program has been written, a CPU (central processing unit) 11 for executing the program, a RAM (random access memory) 12 used for the temporary storing or the like when the program is executed, and the aforementioned interface section 9 for effecting the control of the input from and the output to the outside, and a presentation signal S5 and a request signal S6 to the visual target 1 and a reset signal S7 to the counter 5 are adapted to be put out from the interface section 9. The present apparatus is adapted to be started by a start switch, not shown.

Figure 3:
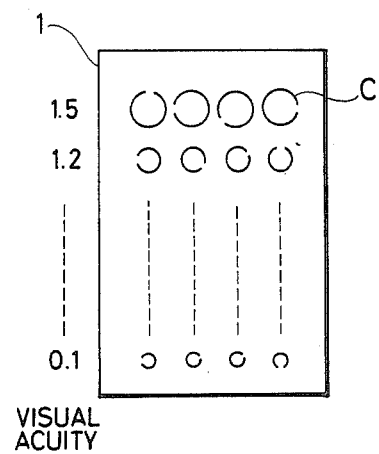
FIG. 3 is a front view of a visual target.

The visual target 1, as shown in FIG. 3, displays Randolt rings C corresponding, for example, to twelve stages of visual acuity from "1.5" to "0.1", and a lamp for each Randolt ring is provided in the interior thereof and may be selectively turned on by the presentation signal S5 from the microcomputer system 8.

Figure 4:
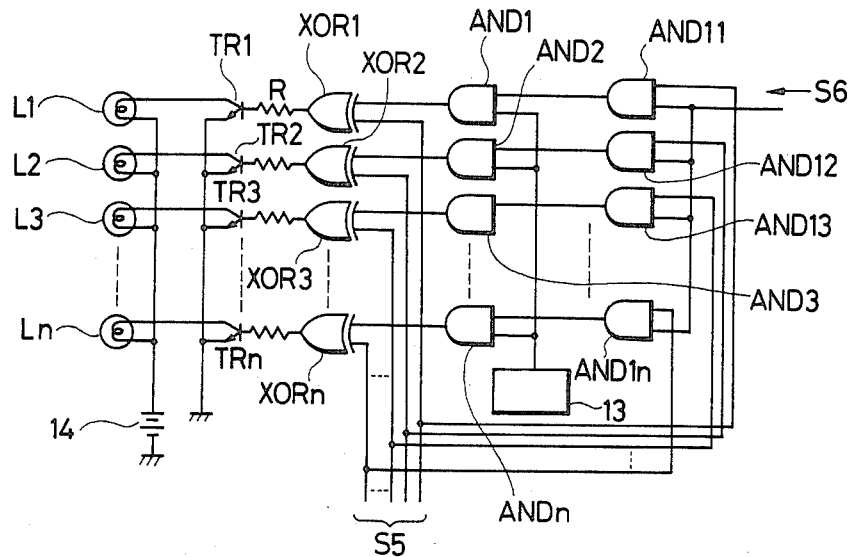
FIG. 4 shows a driving circuit for the visual target.

FIG. 4 shows an example of the electric circuit incorporated in the visual target 1. This electric circuit is comprised of lamps L1-Ln, transistors TR1-TRn, exclusive OR gates XOR1-XORn and AND gates AND1-ANDn and AND11-AND1n provided for the respective Randolt rings C, and an oscillator 13 and a lamp power source 14.

In FIG. 4, the request signal S6 which is the input signal to the AND gates AND11-AND1n and the presentation signal S5 which is the input signal to the exclusive OR gates XOR1-XORn are both at low level in their initial states and therefore, the outputs of the gates XOR1-XORn are at low level and the lamps L1-Ln are turned off.

When the presentation signal S5 is put out from the interface section 9, the input signal, for example, of the exclusive OR gate XOR2 selected assumes high level and therefore the output of the gate XOR2 assumes high level to render the transistor TR2 conductive and turn on the lamp L2. Then, when the request signal S6 assumes high level, the output of the AND gate AND2 also assumes high level and the output of the oscillator 13 is put out through the AND gate AND2 and therefore, by the exclusive or of this output and the input of the OR gate XOR2, an inverted signal from the oscillator 13 is put out to the output side of the gate XOR2, whereby the lamp L2 is turned on and off to request the response input of the subject.

The operation in the above-described embodiment will now be described by reference to the flow chart of FIGS. 5A and B. When the power source 14 has been thrown, the apparatus assumes its initial state and nothing is presented to the visual target 1. When the start switch is depressed, the control flow of FIG. 5 starts in accordance with the program contained in the ROM 10.

Figure 5A:
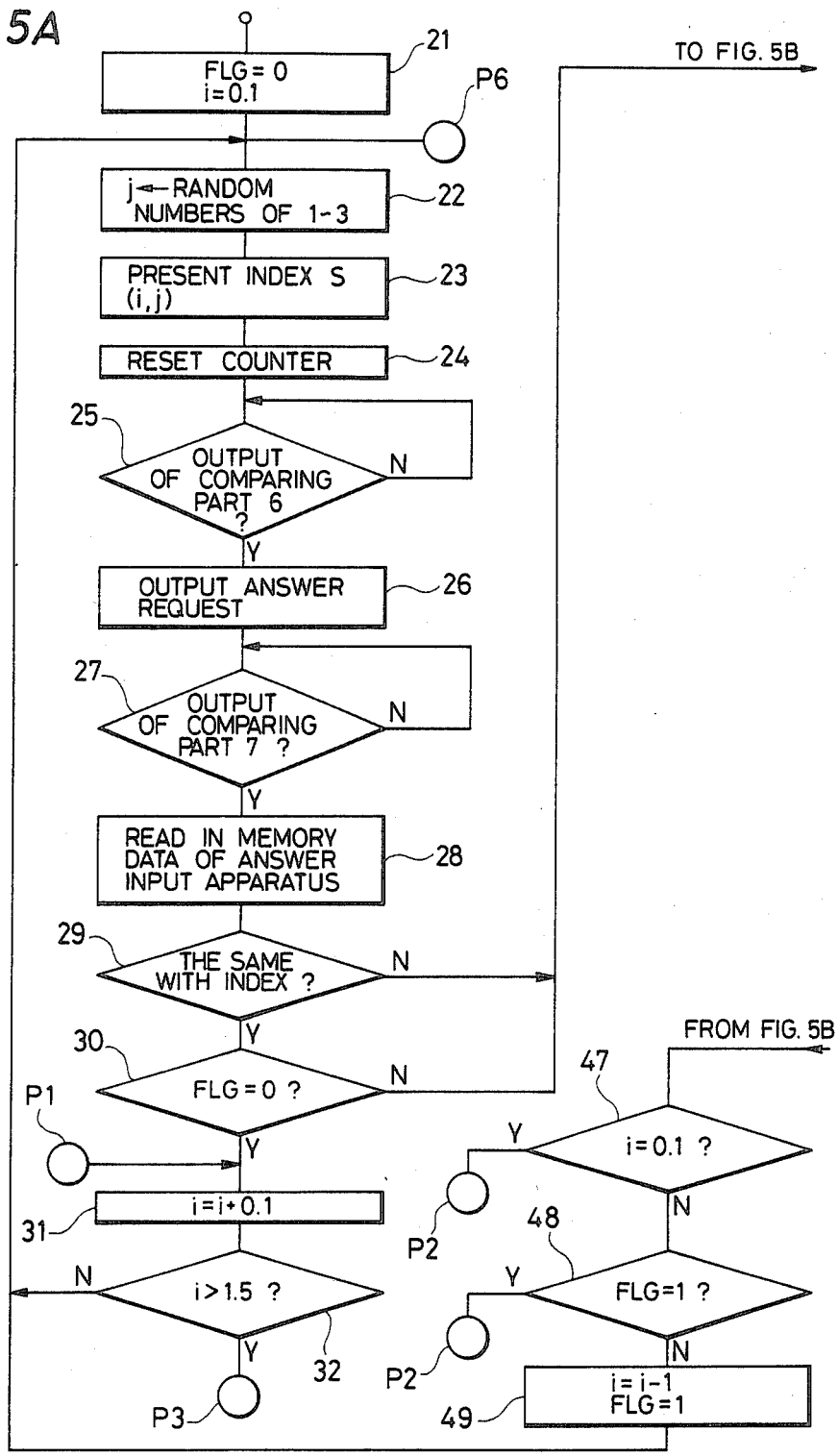
FIGS. 5A and B comprise a flow chart.

In FIGS. 5A and B, symbol FLG represents a flag showing the state of the program, i indicates the visual acuity value, j indicates the number of the visual targets of the same visual acuity value, and the visual target is represented by S(i,j). In this example, there are three sets (j=1,2,3) of visual targets of the same visual acuity value. Reference numerals 21-51 designate operation steps.

The operation steps will first be outlined before they are described in detail.

Here, specifying one j of j=1,2,3 relative to constant i (e.g., i=0.5) and examining it is defined as rough examination (e.g., rough examination of i=0.5), and examining all j's of j=1,2,3 is defined as fine examination (e.g., fine examination of i=0.5).

Figure 5B:
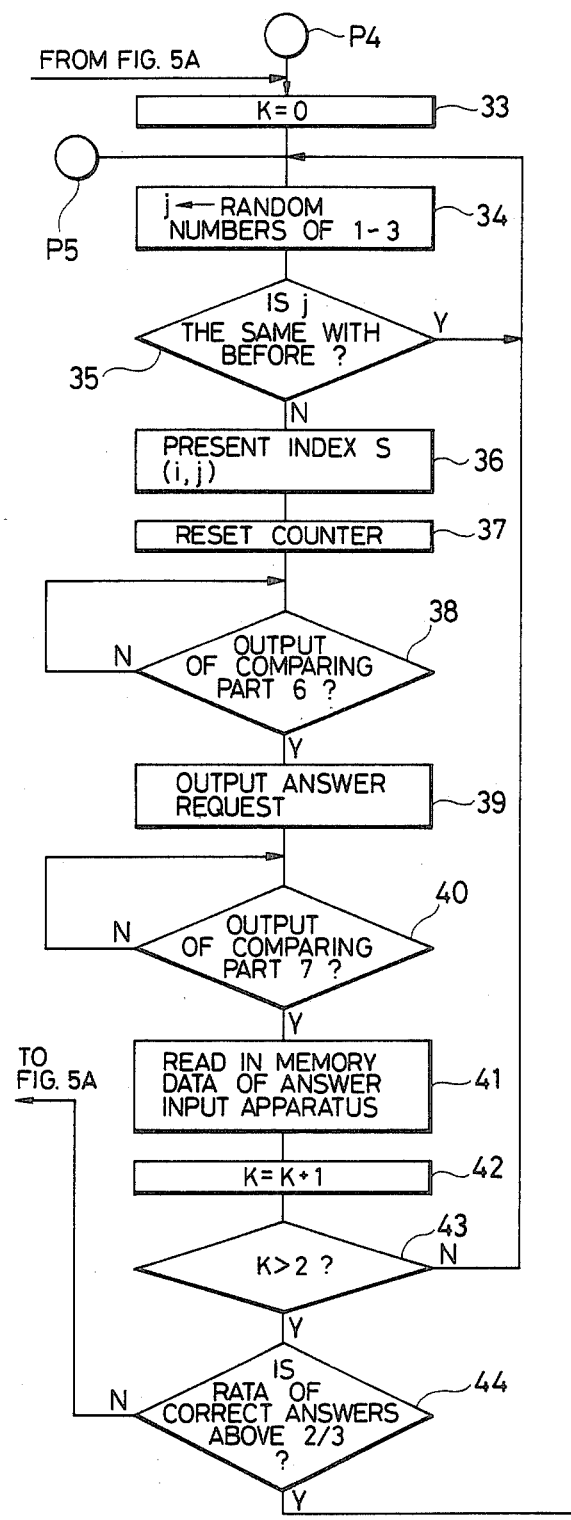
Figure 5B:
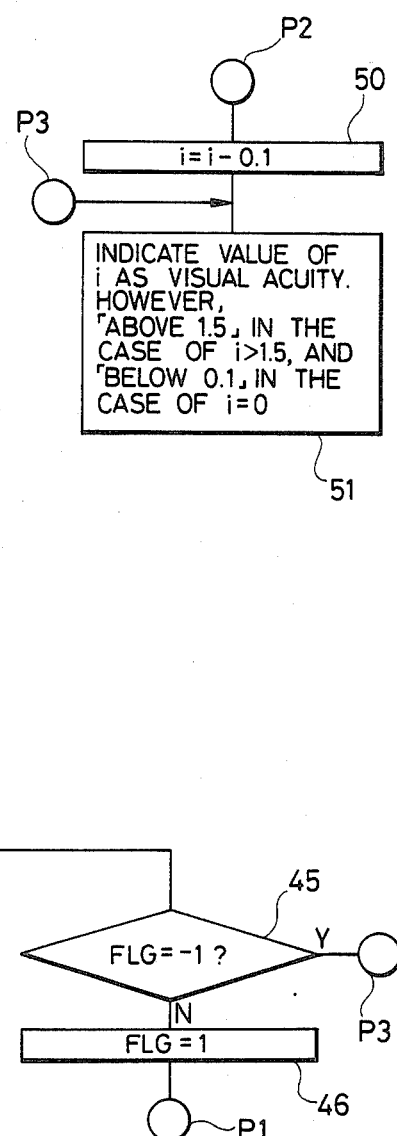

In the operation steps of FIG. 5, when the subject succeeds in the rough examination of i=0.5, the step shifts to the rough examination of i=0.6, and when the subject fails in the rough examination of i=0.5, the step shifts to the fine examination of i=0.5. When the subject succeeds in this fine examination of i=0.5, the step shifts to the fine examination of i=0.6, and when the subject fails in the fine examination of i=0.5, the step shifts to the fine examination of i=0.4. When the subject succeeds in the aforementioned fine examination of i=0.6, the step shifts to the fine examination of i=0.7, and when the subject fails in the fine examination of i=0.6, examination is initiated as the visual power value 0.5. When the subject succeeds in the fine examination of i=0.4, the examination is terminated as the visual acuity value 0.4, and when the subject fails in the fine examination of i=0.4, the step shifts to the fine examination of i=0.3.

The operation steps will hereinafter be described in detail.

First, at step 21, FLG is set to 0 and i is set to i=0.1, and at step 22, random numbers 1-3 are specified for j and S(i,j) is determined. Subsequently, at step 23, the visual target S(i,j) is presented and at step 24, the counter 5 is reset, and immediately thereafter the counter 5 starts counting.

Here, the subject effects a response input from the input switch unit 3 while watching the Randolt ring C of the presented visual target S(i,j). At step 25, the first comparison unit 6 produces an output S3, that is, if there is no response from the subject within a predetermined time, a request signal S6 is put out at step 26 to turn on and off the visual target S(i,j) and request an input again. The subject then waits for the next presentation of the visual target S(i,j) if the response-input content is not due to an inadvertent or erroneous operation, or the subject re-enter an input response from the input switch unit 3 if there is an inadvertent or erroneous operation.

If, at step 27, there is the output S4 of the second comparison unit 7, that is, after a predetermined time elapses, the presentation of the visual target S(i,j) is discontinued and at step 28, the response data of the memory unit 4 in the response input device 2 by the subject is read, and whether or not the response data is coincident with the visual target S(i,j) is examined at step 29. If, at step 29, the input signal S1 is coincident with the visual target S(i,j), the program proceeds to step 30, and if the input signal S1 is not coincident with the visual target S(i,j), the program skips to step 33 because there is presented a visual target S(i,j) of the same i and different j. At this step 33, the examination shifts from rough examination to fine examination. At step 30, whether FLG remains in its initial state is examined and, if it is not in its initial state, that is, if it is not 0, the program skips to step 33. If it is 0, the visual acuity is increased to i=i+0.1, namely, increased by 0.1, at step 31, and the program proceeds to step 32.

At step 32, whether i>1.5 is examined and, if i is less than 1.5, the program skips to step 22. Likewise at step 29, the operations between step 32 and step 22 are repeated until the response input signal S1 is not coincident with the visual target S(i,j).

For example, if at step 29, the response input signal S1 is not coincident with the visual target S(i,j) when i=0.6, the program skips to step 33 and a counter k is repetitively set to 0. Next, at step 34, random numbers 1-3 are set to j with i remaining fixed at i=0.6, and at step 35, whether or not the newly presented visual target is the same as the previously presented visual target S(i,j), that is, whether j is the same, is examined. If the newly presented visual target is the same visual target S(i,j), the program returns to step 34 and random numbers are newly set. If there is obtained a j different from the previous one, the visual target S(i,j) thereof is present at step 36 and simultaneously therewith, at step 37, the counter 5 is reset.

Here, the subject effects a response input by the input switch unit 3 and if, at step 38, the count data signal S2 of the counter 5 is coincident with the first comparison unit 6, a request signal S6 is put out at step 39 and the reentry of a response input is requested when there is an error in the response input or the operation. If, at step 40, there is the output of the second comparison unit 7, the data of the memory unit 4 in the response input device 2 is read at step 41 and at step 42, +1 is effected on k and at step 43, whether or not k is greater than 2 is examined. If, at step 43, k is 2 or less, the program skips to step 34 and the operations between steps 34 and 43 are repeated until the condition that k>2 is satisfied.

When k>2, that is, j=1,2,3, is examined, that is, when examination is completed at all of j=1,2,3 with i remaining fixed, the rate of correct answers thereof is examined at step 44 and if ⅔ or more of the responses are a correct answer, that is, if two or more of three examinations effected at j=1,2,3 with i remaining fixed are given correct answers, whether or not FLG is −1 is examined at step 45 and if FLG is not coincident with −1, 1 is set in FLG at step 46 and the program skips to step 31. The visual acuity is then increased to i=i+0.1, namely, increased by 0.1, and the program proceeds to step 32.

If, at step 44, the rate of correct answers is less than ⅔, whether or not i=0.1 is examined at step 47 and if i is not 0.1, whether or not FLG=+1 is examined at step 48. If FLG is not equal to 1, i is decreased by 0.1 at step 49 and FLG=−1 is brought about, and then the program skips to step 22. When i=0.1 at step 47 and when FLG=1 at step 48, the program skip to step 50 and 0.1 is subtracted from i and, at step 51, the visual acuity value i of the subject is determined and put out.

It is to be understood here that when i=0 at step 51, the visual acuity value is put out as "0.1 or less" and that when i is between 1.5 and 0, the value of i is the visual power value.

If, at step 32, i is greater than 1.5, the program skips to step 51 and at step 51, the visual acuity value of the subject is put out as "1.5 or more"

Thus, in the present program, the magnitude of i, namely, the size of the visual target S(i,j), is presented to the subject while being changed by one stage at a time, and the visual acuity value of the subject is accordingly measured where the rate of correct answers is ⅔ or more. Taking an example, if coincidence is found up to a certain visual acuity value, e.g., "0.8", and at step 29, "0.9" is found, that is, no coincidence is found when i=0.9, the program skips to step 33 and, if the rate of correct answers is ⅔ or less as a result of the program passing through step 44, the program skips to step 47 and since i=0.9, the program shifts to step 48, and since FLG=0, at step 49, the visual target is decreased to "0.8", i.e., by one stage, with i and FLG as i=i−0.1 and FLG=−1, respectively, and the program skips to step 22.

When coincidence is found at step 29, FLG=−1 at step 30 and therefore, the program proceeds from step 33 and, when the rate of correct answers has become ⅔ or more at step 44, the program proceeds to step 45. At step 45, FLG=−1 and therefore, the program skips to p3 and the visual acuity "0.8" is displayed at i=0.8.

If the rate of correct answers is ⅔ or more at step 44, the program skips to step 31 and examination is continued while the examined value is again increased by 0.1 each.

Figure 6:
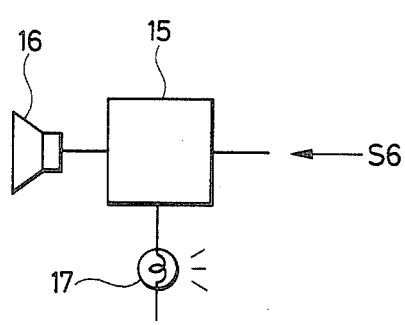
FIG. 6 is a circuit diagram of request means.

Response input request means comprises a speaker 16 connected to a sound producing device 15 as shown in FIG. 6, and can request a response input by appealing to the ear by means of a sound, a synthetic voice or the like. A request lamp 17 may be provided for the purpose of request display separately from the visual target and may be turned on or turned on and off. Both the request by sound and the request by turn-on or turn-on-and-off may be used together.

Figure 7:
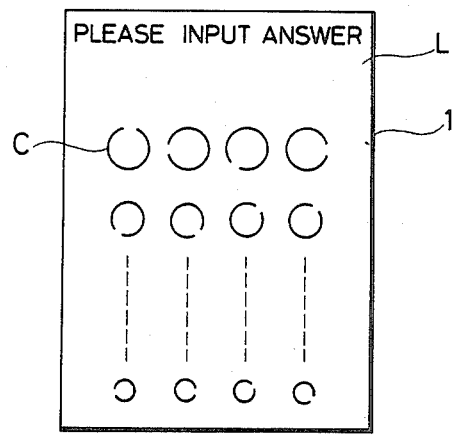
FIG. 7 is a front view of a visual target provided with request means.

Further, as illustrated in FIG. 7, design may be made such that characters L such as "Please input an answer" or other suitable symbols or figures are displayed on the visual target and illuminated from the interior thereof by a lamp or the like when there is a request signal S6. Again in this case, the request by the sound may be used together with the illumination by the lamp or the like.

What is claimed is:
1. An automatic optometer comprising:
   a first visual target for measuring the visual acuity of a subject;
   a response input unit for the subject to input a response corresponding to said visual target;
   a control unit for determining the accuracy of the subject's response input relative to said visual target, and for presenting additional different visual targets;
   a counter, said counter being reset each time a visual target is presented;
   a comparison unit for comparing the output of said counter with a predetermined value; and
   request means for requesting the subject's response input prior to the termination of a predetermined response period, said request means being responsive to an output of said comparison unit.

2. An automatic optometer according to claim 1, further comprising a second comparison unit for comparing the output of said counter with a second predetermined value, and wherein the presentation of the visual target is terminated in accordance with an output of said second comparison unit.

3. An automatic optometer according to claim 1, wherein said request means turns on and off the visual target being presented.

4. An automatic optometer according to claim 1, wherein said request means effects a request by a sound.

5. An automatic optometer according to claim 1, wherein said request means presents a pedetermined display for requesting the subject response.

6. An automatic optometer according to claim 5, wherein said request means flickeringly present a predetermined display.

7. An automatic optometer according to claim 5, wherein said predetermined display include characters.

8. An automatic optometer according to claim 1, wherein a plurality of said visual targets are provided for a predetermined visual acuity value, and said control unit effects a predetermined program of a rough examination based on a single visual target for the predetermined visual acuity value and a fine examination based on a plurality of visual targets for the predetermined visual acuity value.

9. An automatic optometer according to claim 1, further comprising data holding means for holding a response input, wherein when the subject inputs a response prior to the request by said request means, and when the input data is incorrect, the subject may input another response to replace the input response held in said data holding means.

* * * * *

UNITED STATES PATENT AND TRADEMARK OFFICE
CERTIFICATE OF CORRECTION

PATENT NO. : 4,697,895

DATED : October 6, 1987

INVENTOR(S) : Kyoji Sekiguchi, et al.

It is certified that error appears in the above-identified patent and that said Letters Patent is hereby corrected as shown below:

COLUMN 1

Line 20, change "even" to --when--.

Line 24, delete "this".

COLUMN 2

Line 54, change "or" to --use--.

COLUMN 3

Line 49, change "re-enter" to --re-enters--.

COLUMN 4

Line 53, change "skip" to --skips--.

COLUMN 5

Line 16, change "p3" to --P3--.

Line 35, change "the sound" to --sound--.

COLUMN 6

Line 24, change "subject" to --subject's--.

Line 26, change "present" to --presents--.

Line 29, change "include" to --includes--.

UNITED STATES PATENT AND TRADEMARK OFFICE
CERTIFICATE OF CORRECTION

PATENT NO. : 4,697,895

DATED : October 6, 1987

INVENTOR(S) : Kyoji Sekiguchi, et al.

It is certified that error appears in the above-identified patent and that said Letters Patent is hereby corrected as shown below:

IN THE DRAWINGS:

Sheet 4, Figure 5B, Step 44, change "RATA" to --RATE--.

Signed and Sealed this

Second Day of May, 1989

Attest:

DONALD J. QUIGG

Attesting Officer

Commissioner of Patents and Trademarks